United States Patent
Varghese et al.

(10) Patent No.: US 10,092,771 B2
(45) Date of Patent: Oct. 9, 2018

(54) SKIN TREATMENT DEVICE FOR MULTIPHOTON IONIZATION-BASED SKIN TREATMENT

(71) Applicant: KONINKLIJKE PHILIPS N.V., Eindhoven (NL)

(72) Inventors: Babu Varghese, Eindhoven (NL); Rieko Verhagen, Eindhoven (NL); Martin Jurna, Eindhoven (NL); Jonathan Alambra Palero, Eindhoven (NL); Margaret Ruth Horton, Eindhoven (NL); Valentia Bonito, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 314 days.

(21) Appl. No.: 15/034,881

(22) PCT Filed: Oct. 29, 2014

(86) PCT No.: PCT/EP2014/073178
§ 371 (c)(1),
(2) Date: May 6, 2016

(87) PCT Pub. No.: WO2015/071099
PCT Pub. Date: May 21, 2015

(65) Prior Publication Data
US 2016/0271419 A1 Sep. 22, 2016

(30) Foreign Application Priority Data
Nov. 12, 2013 (EP) .................................... 13192534

(51) Int. Cl.
*A61N 5/06* (2006.01)
*A61B 18/04* (2006.01)
(Continued)

(52) U.S. Cl.
CPC .......... *A61N 5/0616* (2013.01); *A61B 18/042* (2013.01); *A61B 18/203* (2013.01);
(Continued)

(58) Field of Classification Search
CPC .......... A61N 5/0616; A61N 2005/0626; A61N 2005/067; A61N 1/44; A61B 18/042;
(Continued)

(56) References Cited

U.S. PATENT DOCUMENTS

2006/0178659 A1 8/2006 Van Hal
2006/0189976 A1 8/2006 Karni
(Continued)

FOREIGN PATENT DOCUMENTS

| RU | 2251990 C1 | 5/2005 |
|---|---|---|
| WO | 2008001284 A2 | 1/2008 |
| WO | 2012106735 A2 | 8/2012 |

OTHER PUBLICATIONS

J. Noack and A. Vogel, "Laser-Induced Plasma Formation in Water at Nanosecond to Femtosecond Time Scales: Calculation of Thresholds, Absorption Coefficients, and Energy Density," IEEE J. Quantum Electron. 35(1999).

(Continued)

*Primary Examiner* — Kevin C Sirmons
*Assistant Examiner* — Leah Swanson (57) ABSTRACT

The invention provides a non-invasive skin treatment device (200) for generating a multiphoton ionization process at a target position (110) in skin tissue (102). The skin treatment device (200) comprises a laser source (105) configured and constructed for generating a laser beam (106), an optical system (109, 112) for focusing the laser beam into the target position below a skin surface (103), and a plasma unit (117) configured and constructed for generating a plasma (100) such that, in use, at least a portion of the plasma penetrates (Continued)

the skin tissue for generating at least one free electron at the target position. The skin treatment device further comprises a control unit (123) configured and constructed for controlling the laser source and the plasma unit such that, in use, at least a portion of the light of the laser beam is absorbed by said at least one free electron generated at the target position, thereby generating the multiphoton ionization process. A result of the use of the plasma in generating the multiphoton ionization process is that an overall laser beam intensity, required to generate the multiphoton ionization process, is reduced as compared to skin treatment devices which generate the multiphoton ionization process using a laser beam only.

13 Claims, 5 Drawing Sheets

(51) Int. Cl.
  *A61B 18/20* (2006.01)
  *A61N 1/44* (2006.01)
  *A61B 18/00* (2006.01)
  *A61N 5/067* (2006.01)
(52) U.S. Cl.
  CPC ........ *A61N 1/44* (2013.01); *A61B 2018/0047* (2013.01); *A61B 2018/00452* (2013.01); *A61B 2018/00583* (2013.01); *A61B 2018/00994* (2013.01); *A61N 2005/067* (2013.01); *A61N 2005/0626* (2013.01)
(58) Field of Classification Search
  CPC ........ A61B 18/203; A61B 2018/00452; A61B 2018/0047; A61B 2018/00583; A61B 2018/00994; A61B 2017/00752; A61B 2017/00761; A61B 2017/00765; A61B 2017/00769; A61B 2017/00747; A61B 2018/00005; A61B 2018/00011; A61B 2018/00017; A61B 2018/00029; A61B 2018/00041; A61B 2018/00458; A61B 2018/00464; A61B 2018/00476; A61B 2018/00577; A61B 2018/00586; A61B 18/20
  USPC .......................................... 604/20
  See application file for complete search history.

(56) References Cited

U.S. PATENT DOCUMENTS

| 2008/0228178 A1 | 9/2008 | Van Hal |
| 2010/0063490 A1 | 3/2010 | Verhagen |
| 2013/0199540 A1 | 8/2013 | Buske |

OTHER PUBLICATIONS

Vogel, Alfred, et al. "Plasma formation in water by picosecond and nanosecond Nd: YAG laser pulses. I. Optical breakdown at threshold and superthreshold irradiance." Selected Topics in Quantum Electronics, IEEE Journal of 2.4 (1996): 847-860.

Gonzalez, Treatment of Acne Scars Using the Plasma Skin Regeneration (PSR) System. Lasers in Surgery and Medicine, 2008. 40: p. 124-127.

Kilmer, S., A pilot study on the use of a plasma skin regeneration device (Portrait® PSR3) in full facial rejuvenation procedures. Lasers Med Sci, 2007 22: p. 101-109.

L. Habbema, R. Verhagen, R. Van Hal, Y. Liu, B. Varghese, "Minimally invasive non-thermal laser technology using laser-induced optical breakdown for skin rejuvenation", Journal of Biophotonics, (2011).

Klaus Dieter Weltmann, Eckhard Kindel, Thomas von Woedtke, Marcel Hähnel, Manfred Stieber, and Ronny Brandenburg, "Atmospheric-pressure plasma sources: Prospective tools for plasma medicine," Pure Appl. Chem., vol. 32, No. 6, pp. 1223-1237, 2010.

Liu Liying, Zhang Jialiang, Wang Dezhen, "An Indirect Method for Measuring Electron Density of Atmospheric Pressure Plasma Jets," Plasma Science and Technology, vol. 1, No. 6, (2009). http://www.iop.org/news/12/apr/page_54993.html.

Rieko Verhagen et al, "Device and method for the treatment of skin and use of the device," Patent WO2008/001584.

E Stoffels, I E Kieft, R E J Sladek, L J M van den Bedem, E P van, "Plasma needle for in vivo medical treatment: recent developments and perspectives", Plasma Sources Sci. Technol. 15 (2006) S169-S180. Source: http://mate.tue.nl/mate/pdfs/6234.pdf.

SKIN TREATMENT DEVICE FOR MULTIPHOTON IONIZATION-BASED SKIN TREATMENT

This application is the U.S. National Phase application under 35 U.S.C. § 371 of International Application No. PCT/EP2014/073178, filed on Oct. 29, 2014, which claims the benefit of International Application No. 13192534.9 filed on Nov. 12, 2013. These applications are hereby incorporated by reference herein.

FIELD OF THE INVENTION

The invention generally relates to the treatment of skin using laser light, and more particularly to a skin treatment device for generating a multiphoton ionization process in a target position in skin tissue.

BACKGROUND OF THE INVENTION

The desire to maintain a youthful appearance by preventing or reducing wrinkles in the skin is an important issue in human society. Many techniques have been designed to achieve the above issue. One of the techniques known from the published international patent application WO 2008/001284 A2 is to create a focal spot in a dermis layer of the skin to be treated. Said WO application discloses a skin treatment device with a laser source and focusing optics, wherein the power of the laser is selected such that Laser Induced Optical Breakdown (LIOB) affects the skin in order to stimulate re-growth of skin tissue and reduce wrinkles. This LIOB is based on strong non-linear absorption of the laser light by the skin tissue, which occurs above a certain threshold value of the power density of the laser light in the focal spot of the laser beam. This strong absorption causes a localized plasma that is able to damage or even remove tissue at the location of said plasma. This is caused by secondary, primarily mechanical, effects such as rapid expansion of the generated plasma. This effect is very local because, below the threshold, there is zero or very little linear and non-linear absorption while, above the threshold, a plasma is generated which even more strongly absorbs the laser light. In other words, effects such as LIOB only occur in the focal spot, while above and below the focal spot no or very much weaker effects occur. This means that, for example, the epidermis may easily be safeguarded against undesired effects or damage.

Laser skin ablation through a multiphoton ionization process, such as for example laser induced optical breakdown, requires high light intensities of the order of $10^{13}$ W/cm$^2$. Due to a very high photon flux (typically $>10^{31}$ cm$^{-2}$ s$^{-1}$), multiple (N) photons with an energy of hv at the wavelength of $\lambda$ behave like a photon of energy Nhv and interact with an electron to free it from the valence band. This requires the total energy of the absorbed photons to be greater than the ionization potential (Nhv>$\Delta$). The generation of this so-called seed electron or free electron by ionization requires multiple photons (N) having the same polarization confined in space (focal volume) and in time (~nano to femto seconds) with a total energy exceeding the ionization potential (Nhv>$\Delta$) of the material. Achieving a multiphoton ionization process deep inside the skin is a challenging task.

US2013/0199540 A1 discloses a device for plasma treatment of living tissue, with a plasma source for generating an atmospheric plasma jet, with a support device for a body part comprising the tissue to be treated, with a movement device for moving the plasma source relative to the surface of the tissue, and with a control device for controlling the movement device and for controlling the operation of the plasma source, wherein the control device has means for adjusting the plasma output as a function of the position relative to the tissue. In an embodiment, the device has optical means for measuring a distance between the front end of the outlet opening of the plasma jet and the object to be treated. Said optical means comprise a laser source generating a laser beam which is directed towards the object to be treated through a channel formed in the internal electrode of the plasma generator. The laser beam reflected by the object is directed in opposite direction through the channel and is reflected to a photosensor by means of an output coupling mirror. In another embodiment, before, during and after the plasma treatment a heat treatment, light treatment and/or laser treatment can be carried out. These additional treatments can support and extend the way in which the plasma treatment works.

SUMMARY OF THE INVENTION

An object of the invention is to provide a non-invasive skin treatment device for generating a multiphoton ionization process in a target position in skin tissue, by means of which the multiphoton ionization process is produced at a relatively low light intensity.

According to the invention, this object is achieved by a skin treatment device comprising:

a laser source configured and constructed for generating a treatment laser beam, an optical system configured and constructed such that, in use, the treatment laser beam is focused into a focal spot in the target position in the skin tissue, a plasma unit configured and constructed for generating a plasma such that, in use, at least a portion of the plasma penetrates the skin tissue and generates at least one free electron in the target position in the skin tissue, and a control unit configured and constructed for controlling the laser source and the plasma unit, wherein the laser source and the optical system are configured and constructed such that, in use, a power density of the treatment laser beam in the focal spot in the skin tissue is below a first power density threshold for the skin tissue, above which a free electron is generated in the skin tissue by absorption of photons present in the treatment laser beam, and the power density of the treatment laser beam in the focal spot is above a second power density threshold for the skin tissue, above which an avalanche ionization process is generated in the skin tissue by Inverse Bremsstrahlung absorption by a free electron of photons present in the treatment laser beam.

The invention is based on the insight that a laser beam intensity, i.e. a power density of the laser beam in the focal spot, required for generating seed electrons or free electrons inside skin tissue is significantly higher as compared to a laser beam intensity required to generate a subsequent avalanche ionization process in multiphoton ionization processes. The inventors have realized that by providing a plasma near the skin surface, the overall laser beam intensity required for generating a multiphoton ionization process is reduced. The plasma provided near the skin surface penetrates the skin tissue and generates at least one free electron at the target position. Said at least one free electron at the target position generated by the plasma subsequently acts as the seed electron for the ionization process. At least a portion of the light of the treatment laser beam, which is focused into the target position, will be absorbed by the seed electron generated by the plasma to initiate the avalanche ionization process inside the skin tissue. So, due to the presence of the plasma which generates the seed electron for the multiphoton ionization process, the treatment laser beam intensity required for generating the multiphoton ionization process is reduced as compared to a multiphoton ionization process generated solely by laser light without the presence of a plasma.

A multiphoton ionization process to create lesions inside the skin tissue requires high light intensities, i.e. a high power density of the laser beam, for example of the order of $10^{13}$ W/cm$^2$. The multiphoton ionization process actually is a two-step process, wherein in a first step a free electron or seed electron is generated via absorption of multiple photons having a same polarization state. In a second step, an avalanche ionization process is generated by Inverse Bremsstrahlung absorption of photons by the seed electron. The laser beam intensity threshold required to generate the seed electron is significantly higher as compared to the laser beam intensity threshold required to generate the avalanche ionization process. The generation of the seed electron by multiphoton ionization is a function of both the medium characteristics and the beam characteristics. When polarized light is focused inside turbid media like skin, the fraction of photons having the same polarization in the focal spot is significantly reduced. This is caused by a change in polarization of (some of) the photons due to high NA focusing, multiple scattering and birefringence of the skin tissue. The relatively high laser beam intensity threshold, required for generating the multiphoton ionization process by means of the known skin treatment devices, should at least partially compensate for the reduction in the number of photons with the same polarization available for multiphoton ionization in the target position in the skin tissue. This relatively high intensity threshold required for initiating and generating this multiphoton ionization process also increases the risk of collateral damage to the surrounding tissue and significantly increases the overall power requirements of the known skin treatment devices. By using a plasma which is generated near the skin surface and which penetrates the skin tissue to generate at least one free electron at the target position in the skin tissue, a reduction of the treatment laser beam intensity required for generating the multiphoton ionization process is achieved to a level well below the laser beam intensity threshold required when using the known skin treatment devices.

In an embodiment of the skin treatment device according to the invention, the control unit is configured and constructed to activate the laser source to generate the treatment laser beam only after the plasma has been generated by the plasma unit. As such, the plasma generated by the plasma unit is able to penetrate the skin tissue to provide the at least one free electron at the target position.

In a further embodiment of the skin treatment device according to the invention, the skin treatment device further comprises an electric field generator controlled by the control unit, wherein the electric field generator is configured and constructed for generating, in use, an electric field to guide the plasma towards the target position. In addition to guiding the plasma towards the target position, the electric field may be configured and constructed to also force at least some of the plasma into the skin tissue in order to reach the target position and provide the at least one free electron at the target position. In this embodiment, the control unit may be configured and constructed for adjusting a strength of the electric field generated by the electric field generator in order to achieve a desired penetration depth and/or a desired penetration speed of the plasma towards the target position. When, for example, the treatment laser beam of the skin treatment device is scanned over the skin surface for the treatment of a relatively large area, the strength of the electric field may be adjusted or adapted to comply with the scanning speed used by a user during the treatment.

In an embodiment of the skin treatment device according to the invention, the plasma unit comprises a plasma channel wherein the plasma is generated. In this embodiment, in use, a fluid flows through the plasma channel towards the skin surface, at least a portion of the fluid being converted into the plasma in the plasma channel. The fluid flowing through the plasma channel towards the skin surface will result in a plasma flow or even a plasma jet, which may be directed to the surface of the skin tissue and which may also be used to improve the penetration depth and penetration speed of the plasma towards the target position. In a further embodiment of the skin treatment device according to the invention, the plasma channel comprises an outlet for emitting the plasma towards the skin surface, the outlet being configured and constructed for directing the plasma towards the target position inside the skin tissue. The outlet may, for example, comprise a nozzle from which the plasma jet is emitted and which may be used to direct the plasma jet towards the target position inside the skin tissue. When the skin treatment device is in use, the fluid may flow through the plasma channel at a flow rate between 2 and 20 standard liter per minute or, for example, at a flow rate between 5 and 10 standard liter per minute. Preferably, the fluid comprises a noble gas such as, for example, Argon. Using a noble gas will prevent any unwanted chemical reactions from taking place during the generation of the at least one free electron or seed electron at the target position by the plasma. The use of, for example, Argon gas results in a relatively cost-effective solution, because Argon gas is relatively inexpensive compared to other noble gasses.

In an embodiment of the skin treatment device according to the invention, the plasma unit comprises plasma generation means at or near the skin surface for generating the plasma at or near the skin surface. Such plasma generation means may, for example, be electrodes arranged at or near the skin surface. Such electrodes may, for example, ionize the ambient air to generate the plasma at or near the surface of the skin.

In an embodiment of the skin treatment device, the plasma unit is configured to generate a direct plasma, an indirect plasma and/or a hybrid plasma. In a direct plasma, the skin tissue functions as an electrode and an electric current flows through the body. The plasma unit may, for example, comprise a dielectric barrier discharge device. The fluid which is ionized in such a direct plasma is, for example, ambient air in the neighborhood of the dielectric barrier discharge device. An indirect plasma is generated in a position away from the skin tissue, using, for example, two electrodes through which a fluid flows to the target position. This fluid may, for example, be air or preferably a noble gas. In such an embodiment, the plasma unit may, for example, comprise a plasma torch. The hybrid plasma has a mode of generation of a direct plasma and has properties of an indirect plasma. Due to the use of a grounded electrode net with a low electrical resistance, no electric current flows through the skin tissue. The plasma unit may, for example, comprise a Barrier coronal discharge device.

In an embodiment of the skin treatment device, the plasma generated by the plasma unit comprises a non-thermal plasma. In a non-thermal plasma or "cold" plasma only a fraction of the fluid is ionized. A non-thermal plasma is preferred for safety reasons, because it typically has a relatively low temperature, often around room temperature, while it is sufficiently ionized to generate the at least one free electron at the target position. Alternatively, a hot plasma may be used.

In an embodiment of the skin treatment device, the optical system is configured and constructed to generate a plurality of focal spots in a plurality of target positions inside the skin tissue, the plasma unit being configured and constructed to generate the plasma near a skin surface such that, in use, at least a portion of the plasma penetrates the skin tissue for generating at least one free electron in each of said plurality of target positions. In this embodiment, the penetration of the plasma into the skin tissue may occur over a relatively large area of the skin surface. A single plasma unit may be used to generate the at least one free electron in each of said plurality of target positions, which may be distributed over a relatively large treatment area. For example, the skin treatment device may comprise a scanning system by means of which the treatment laser beam is scanned and focused in a plurality of adjacent target positions inside the skin tissue. The scanning system may, for example, comprise a scanning mirror arrangement arranged inside the skin treatment device. Such a skin treatment device providing a relatively large treatment area may comprise a single plasma unit which covers substantially the whole treatment area and which provides the at least one free electron at each of the plurality of target positions inside the treatment area. Alternatively, the skin treatment device may comprise more than one plasma unit. The use of more than one plasma unit is advantageous, for example, when the treatment area becomes too large to be covered by a single plasma unit, or when the scanning speed of the scanning system of the skin treatment device is relatively high such that the plasma preferably is generated closer to the target position.

It should be noted that items bearing the same reference numbers in different Figures have the same structural features and the same functions, or represent the same signals. Where the function and/or structure of such an item has been explained, there is no necessity for repeated explanation thereof in the detailed description.

DETAILED DESCRIPTION OF EXAMPLES

Figure 1:
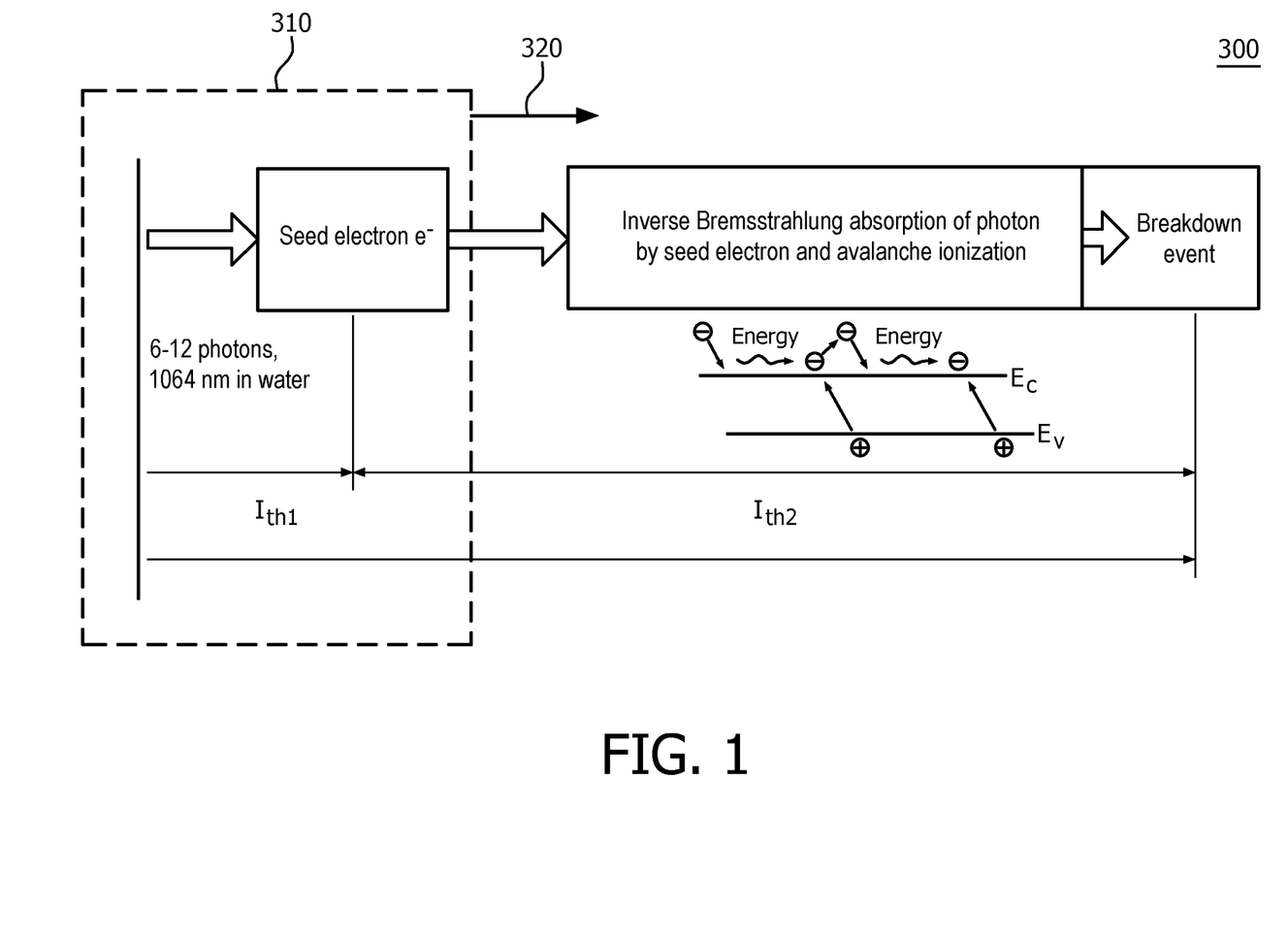
FIG. 1 shows a schematic diagram of the light induced optical breakdown process.

FIG. 1 shows a schematic diagram 300 of the light induced optical breakdown process. Multiphoton ionization to create lesions inside the skin tissue requires high light intensities—of the order of $10^{13}$ W/cm$^2$. As indicated before and as shown in FIG. 1, the multiphoton ionization process actually is a two-step process in which, in a first step 310, a seed electron is created via absorption of multiple photons having a same polarization state. In a second step 320, an ionization avalanche is generated by Inverse Bremsstrahlung absorption of photons by the seed electron. The laser beam intensity threshold $I_{th1}$, i.e. a first power density threshold characteristic for the skin tissue, to create the seed electron in the skin tissue is significantly higher than the laser beam intensity $I_{th2}$, i.e. a second power density threshold characteristic for the skin tissue, to generate the ionization avalanche in the skin tissue. The relatively high laser beam intensity threshold $I_{th1}$ for initiating the multiphoton ionization process is typically required for creating the seed electron. The requirement that multiple photons (between 6 and 12 photons) with the same polarization have to be absorbed to free the seed electron while skin properties and high NA focusing depolarize part of the focused laser beam, results in access of laser light that needs to be focused in the target position 110 to free the seed electron. As soon as the seed electron is freed in the target position 110, the seed electron will absorb part of the Inverse Bremsstrahlung of the photons provided by the laser beam to generate the avalanche ionization process. According to the invention, by using a plasma provided or generated at or near the skin surface and allowing said plasma to penetrate the skin tissue to provide at least one free electron at the target position, a reduction will be achieved of the laser beam intensity for generating the multiphoton ionization process. In particular, the multiphoton ionization process is achieved by configuring and constructing a laser source and an optical system such that, in use, a power density (W/cm$^2$) of the treatment laser beam in the focal spot of the treatment laser beam in the skin tissue is below said first power density threshold ($I_{th1}$) for the skin tissue (102), and the power density (W/cm$^2$) of the treatment laser beam (106) in the focal spot is above said second power density threshold ($I_{th2}$) for the skin tissue (102).

Figure 2:
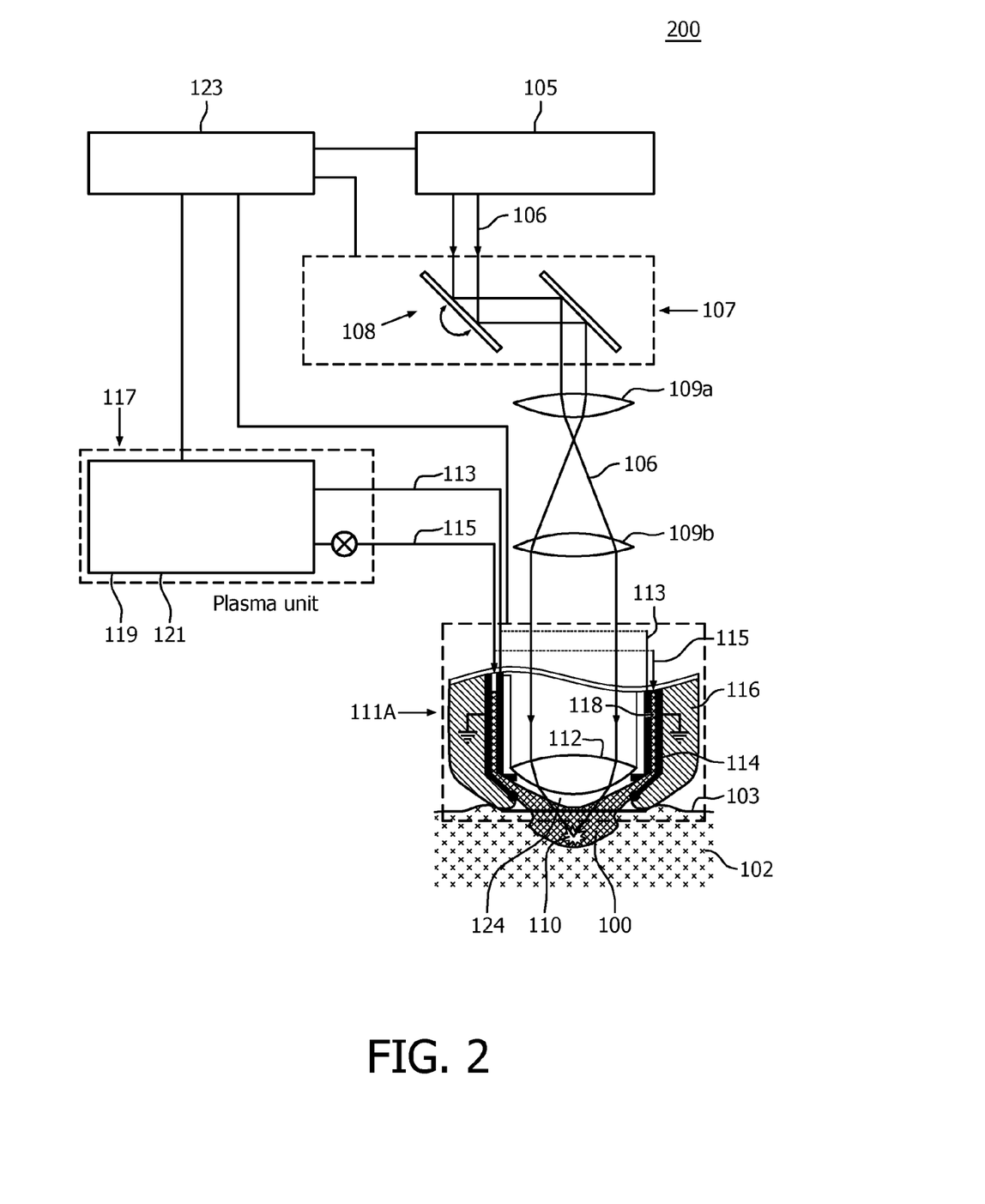
FIG. 2 diagrammatically shows a first embodiment of the skin treatment device according to the invention, FIGS. 3A, 3B and 3C diagrammatically show, respectively, a second, a third and a fourth embodiment of the skin treatment device according to the invention.

FIG. 2 diagrammatically shows a first embodiment of the skin treatment device 200 according to the invention. This first embodiment as shown in FIG. 2 comprises a laser source 105, a laser scanning unit 107, a beam shaping system 109, a plasma unit 117, a plasma-laser focusing unit 111A and a control unit 123. The laser source 105 emits a laser beam 106 in the form of laser pulses, e.g. ultra-short laser pulses from a Nd:YAG laser with a wavelength of the emitted light of 1064 nanometers and a pulse duration between 1-1000 picoseconds. Of course also a laser beam 106 having a different wavelength may be used. The skin treatment device 200 as shown in FIG. 2 further comprises a laser scanning unit 107 which is optional for such skin treatment devices 200. Such laser scanning units 107 often comprise one or more movable mirrors 108 which are configured to scan the laser beam 106, for example, within a treatment area (not indicated) of the skin treatment device 200. The one or more movable mirrors 108 may be arranged on a rotating wheel (not shown, but often indicated as axicon wheel), or may be mirrors 108 which are movable in one, two or three dimensions. The beam shaping system 109 is configured to modify the profile of the laser beam 106, e.g. expand the laser beam 106 using an expansion lens 109a, and subsequently focus the expanded laser beam 106 into the skin tissue 102 using a collimating lens 109b. The plasma unit 117 comprises a power supply 119, a gas source 121 and a plasma channel 118. The power supply 119 provides, for example, high-voltage electrical energy, wherein the electrical energy may, for example, be frequency-modulated in a frequency output range from Direct Current (further also indicated as DC) to Radio Frequency (further also indicated as RF). The gas source 121 provides a fluid, for example, a gas which is converted into plasma 100 in the plasma channel 118, using the power supply 119. One example of such a gas may be Argon which in the current embodiment flows into the plasma channel 118. However, also other gasses may be used, preferably other noble gasses. Alternatively, the plasma unit 117 may ionize the ambient air at or near the skin surface 103 to generate the plasma at or near the skin surface 103.

In the current embodiment, at least a part of the Argon gas is converted into plasma 100 to generate a plasma jet above the skin surface 103. The plasma 100 subsequently penetrates into the skin tissue 102, providing free electrons inside the skin tissue 102 at the laser target position 110. The plasma-laser focusing unit 111A in the skin treatment device 200 according to the invention comprises a laser focusing system 112 and plasma 100 generation and directing systems. The laser focusing system 112, for example, consists of a single high-NA focusing lens 112 to focus the laser beam 106 into a target position 110 below the skin surface 103. The plasma generation system comprises an anode 113, which is arranged at a central part of the plasma channel 118 which is subsequently surrounded by a grounded cathode 114, for example, covering part of the inner wall of the plasma channel 118. Finally, the embodiment of the plasma-laser focusing unit 111A comprises an insulated treatment head 116 which, in use, is in contact with the skin surface 103.

In the embodiment shown in FIG. 2, the laser focusing system 112 is a hydrophobic convex-shaped focusing lens 112, preferably having a refractive index close to that of skin (e.g.: PMMA, CR-39). During use of the embodiment, an optical coupling medium 124 may be arranged between the convex-shaped focusing lens 112 and the skin surface 103, such as a thin layer of low-viscous oil 124 preferably in a thickness of the order of microns and with an index of refraction again close to the index of refraction of the skin and close to the index of refraction of the convex-shaped focusing lens 112. Such an optical coupling medium 124 may be applied, for example, before the laser-based skin treatment is started. In use, the convex shaped focusing lens 112 contacts the skin surface 103 with its convex surface and locally stretches the skin surface 103. The presence of the optical coupling medium 124 will further flatten the skin surface 103 to reduce micro-roughness by filling microscopic gaps still present in the stretched skin surface 103. This filling of the microscopic gaps by the optical coupling medium 124 can be attributed to a capillary effect and will improve the coupling of the laser beam into the skin tissue 102.

The skin treatment device 200 further comprises the control unit 123 which controls the laser source 105 and the plasma unit 117. The control unit 123, for example, controls an output power of the laser source 105, and controls scanning parameters of the laser scanning unit 107, and also controls the laser focusing system 112, for example, to determine a depth of the target position 110 at which the laser beam 106 is focused in operation. The control unit 123 also controls the plasma unit 117, for example, a gas flow 115 from the gas source 121 into the plasma channel 118 and, for example, a plasma voltage applied in the plasma channel 118 to generate the plasma jet towards the skin surface 103.

The skin treatment device 200 may further comprise an electric field generator (not shown) for guiding the plasma 100, for example, towards the target position 110. Such an electric field generator may further be used to accelerate the ions in the plasma 100 and thereby push or drive the plasma into the skin tissue 102. This electric field generator may thus be used to increase a penetration speed of the plasma 100 into the skin tissue 102 and/or may be used to increase a penetration depth of the plasma 100 into the skin tissue 102.

The invention uses the fact that the skin transmits electromagnetic radiation that is to be focused into a very small focal spot in the dermis. To maximize this effect, a wavelength of the light is between 800 and 1100 nm; for example, a Nd:YAG laser is used with emission wavelength at 1064 nm and 1-1000 ps pulse duration. In this range, transmission is relatively high and scattering and linear absorption are low. It is however not excluded to use other wavelengths.

In particular, the predetermined pulse time is between 100 ps and 10 ns. In this range, the plasma generated by the multiphoton ionization is very local, i.e. has a small spatial extension, which minimizes the risk of unintended damage to surrounding tissues. However, other pulse times, e.g. in the range of about 100 fs to 100 ps, may also be used, and even in the ns and ms ranges.

Typically, the deliverable energy level in the laser beam pulse is between 0.1 and 10 mJ, measured at the surface of the skin. Such energy levels have turned out to be useful in the treatment, i.e. generate sufficient damage to stimulate new tissue growth. More specifically, the energy level is between about 0.5 and 5 mJ, and typically about 1 mJ. However, other energy levels are not excluded, such as levels up to about 20 mJ for large treatment depths of up to 2 mm. In the above energy level indications, the energy is measured at the surface of the skin, i.e. it relates to the energy actually emitted into the skin.

In all of the above it is to be understood that instead of a single pulse, it is also possible to provide a number of pulses, as long as the pulses generate a multiphoton phenomenon.

The skin comprises multiple layers with different optical properties. The epidermis is composed of the outermost layers and forms a waterproof protective barrier. The outermost layer of the epidermis is the stratum corneum which, due to its microscopic fluctuations in roughness, impedes the coupling of light between the skin treatment device 200 and the skin tissue 102. Underneath the epidermis, the dermis is situated. The dermis comprises the collagen fibers at which the skin treatment typically is aimed.

Typically, the skin treatment device 200 has a numerical aperture (NA) of at least 0.2, preferably at least 0.4. Such values for the numerical aperture relate to safety for the overlying skin layers, in particular the epidermis. Since, in particular, the epidermis contains many chromophores such as melanin, the residual linear absorption in the epidermis is not negligible. Hence, it is advantageous to keep the fluence, or energy density, in such layers sufficiently low. This may be achieved by providing a strongly focused laser beam, i.e. with a large angle of convergence, and hence with a large numerical aperture of the optical system. The laser beam then covers a sufficiently large area to maintain the fluence in the epidermis within an acceptable range. In particular, the fluence in the epidermis should be at most 3 J/cm2. Note that the desired numerical aperture depends on the treatment depth and on the actual energy in the pulse. Model calculations show that a numerical aperture of at least 0.4 suffices for a treatment depth of 0.5 mm and an energy of 1 mJ in the plasma (in the focus), while higher NAs are needed for higher energy levels and smaller treatment depths, and vice versa.

Note that the NA needed for large treatment depths is of course smaller than that for small treatment depths, because of the larger distance to the epidermal layers that are not to be damaged. However, the total intensity and energy needed to achieve sufficient multiphoton ionization at larger treatment depths becomes larger, due to residual absorption and scattering in the overlaying layers.

For typical treatment depths, a numerical aperture of at least 0.7 may be advantageous to provide an optimal intensity in the focus, and to minimize the thermal load on the superficial layers of the skin.

In particular, a fluence of the laser beam pulse is at the most 3 J/cm2 in the skin between the surface of the skin and the dermis layer. Such a fluence is deemed safe for said skin layers. Together with the preferred energy levels for the laser beam pulse, this leads to preferred laser beam apical angles of, in particular, at least 11° (half angle) for 1 mJ and a treatment depth of 0.5 mm. In dependence on the desired treatment depth and pulse energy, the skilled person can easily determine the preferred apical angle, or the related numerical aperture.

Typically, the treatment depth is between 0 and 2 mm, more particularly between 0.2 and 1.5 mm, below the surface of the skin. This is based on a typical total thickness of the epidermis with the stratum corneum, in the face, of between 0.06 and 0.2 mm and a typical thickness of the dermis layer of 2 mm. Hence, the dermis may be found at a depth of between 0.2 and about 2 mm. A treatment depth of between 0.5 and 1.5 mm offers a range that allows treatment of the dermis with sufficient expansion yet without any risk for the surrounding layers such as the epidermis. In particular cases, the epidermis and/or dermis may be thinner or thicker, or may be present at a slightly different depth, such as on other parts of the body, e.g. the hands. In that case, the skilled person will easily be able to determine the depth and/or thickness of the dermis, and configure the device accordingly. A different treatment depth may then be set after establishing the depth and thickness of the dermis layer. It is also possible to use or include a device for automatic determination of the thickness of the dermis and/or epidermis, such as an ultrasonographic device, for example the Stiefel Cutech "Dermal depth Detector", or alternatively an OCT device (optical coherence tomography).

Figure 3A:
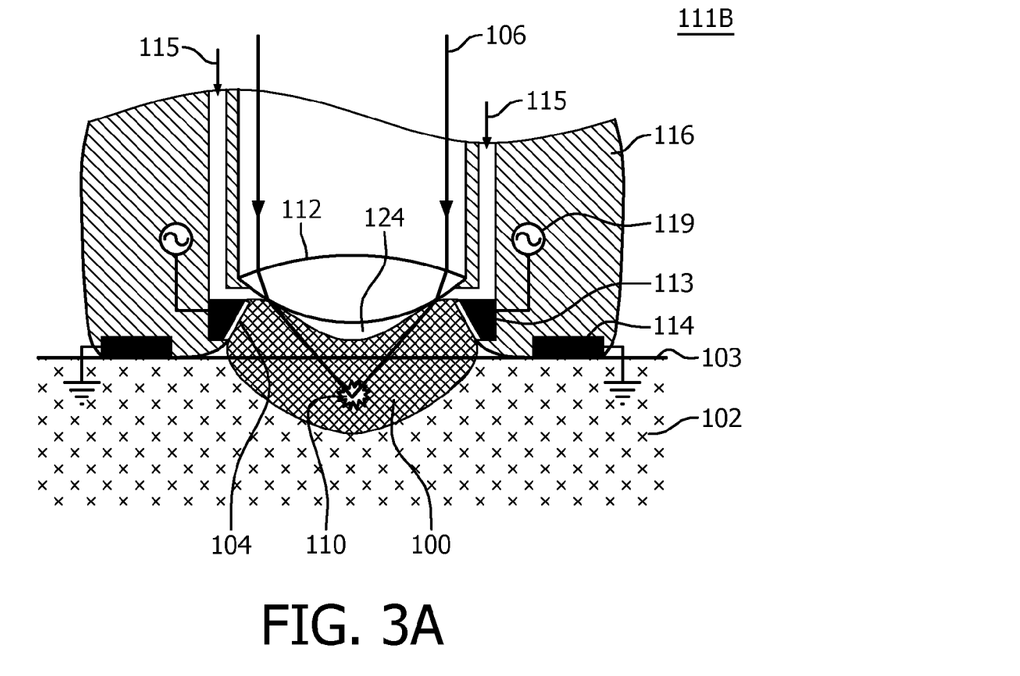
Figure 3B:
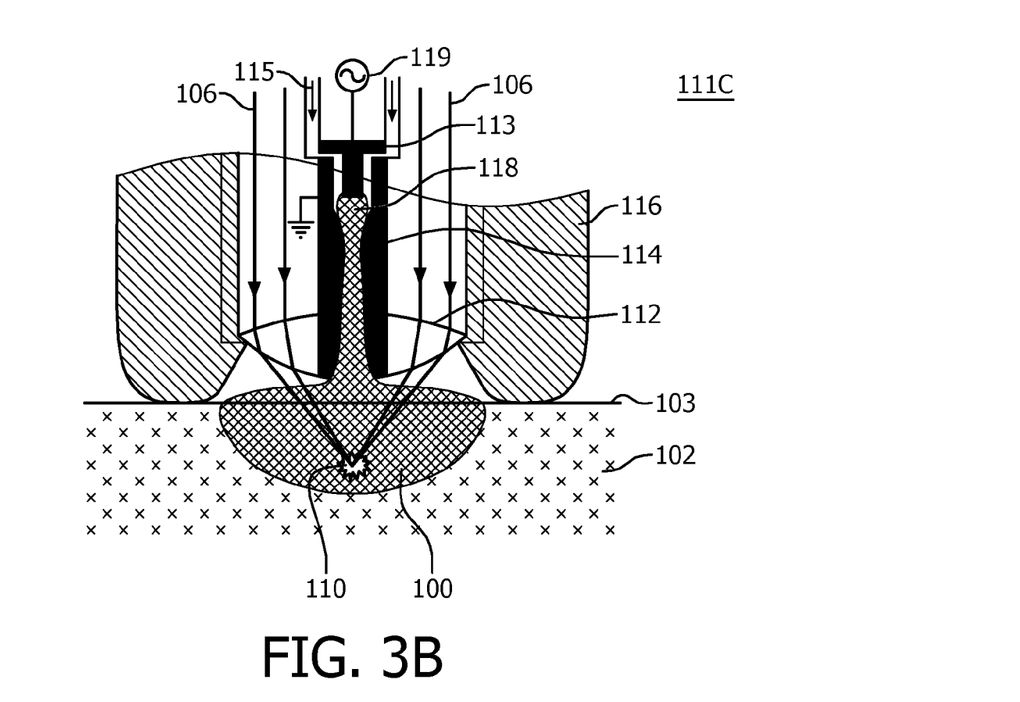
Figure 3C:
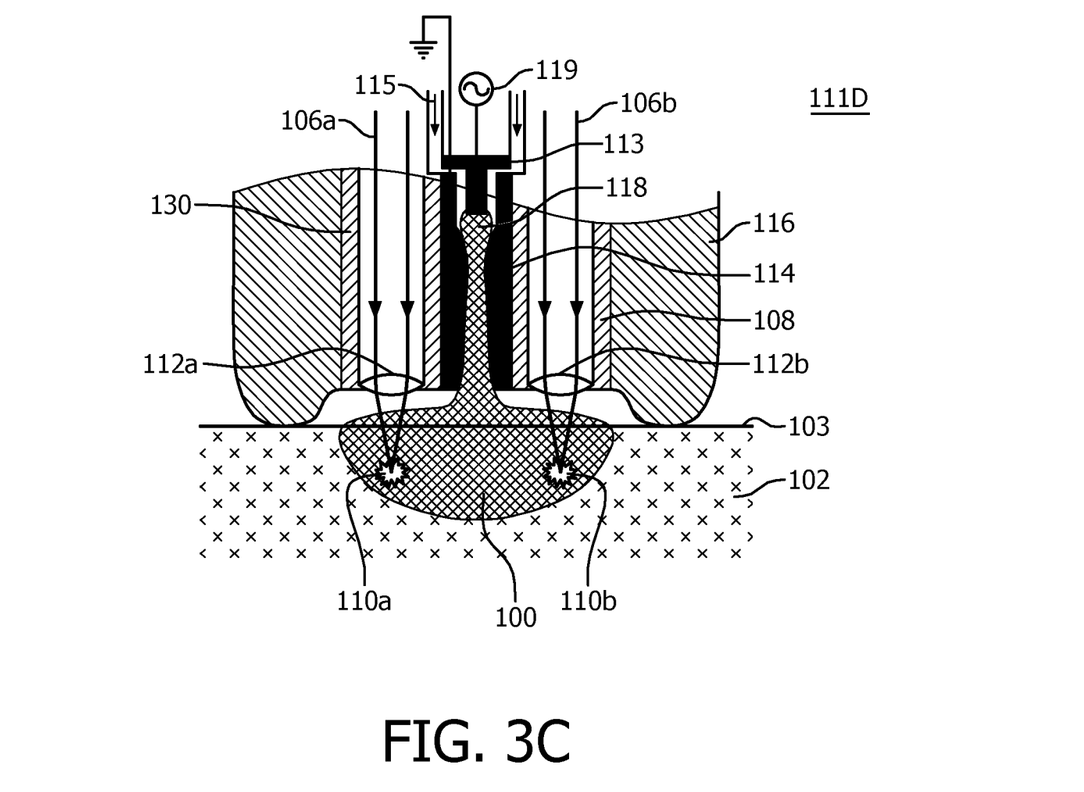

FIGS. 3A, 3B and 3C diagrammatically show a second, third and fourth embodiment of the skin treatment device 200 according to the invention. In FIGS. 3A, 3B and 3C, only the plasma-laser focusing units 111B, 111C, 111D, respectively, of the different embodiments are shown. All other elements such as the laser source 105, laser scanning unit 107, beam shaping system 109, plasma unit 117, and control unit 123 may be similar or identical to the embodiment shown in FIG. 2.

In contrast to the embodiment shown in FIG. 2, the plasma-laser focusing unit 111B shown in FIG. 3A comprises a dielectric barrier discharge system for generating the plasma 100. Dielectric-barrier discharges are characterized by the presence of one or more dielectric layers 104 in the discharge path extending from the anode 113 via the discharge space to the cathode 114. Different configurations of anode 113, cathode 114 and dielectric layers 104 are possible. For example, a planar configuration comprises parallel plates forming the anode 113 and cathode 114, which are separated by the dielectric layer 104 and the discharge space. Alternatively, a cylindrical configuration may be used in which the anode 113 and the cathode 114 are coaxially arranged (not shown) and a dielectric tube (not shown) is arranged between them within which the discharge (and thus the plasma 100) is generated. In FIG. 3A, the plasma 100 is formed between the anode 113 comprising a dielectric layer 104 attached thereto and the skin surface 103 which is electrically coupled to the grounded cathode 114.

In the third embodiment of the plasma-laser focusing unit 111C of the skin treatment device 200 as shown in FIG. 3B, the plasma-laser focusing unit 111C comprises a centered anode 113 at least partially surrounded by a tubular cathode 114 forming a plasma channel 118 positioned in the center of the plasma-laser focusing unit 111C. In the current embodiment, the laser beam shaping system 109 (not shown in FIG. 3B) generates an annular-shaped laser beam 106 which passes through the plasma-laser focusing unit 11C around the plasma channel 118. A single-focus lens system 112 is present for focusing the annular laser beam 106 into a target position 110 inside the skin tissue 102.

In the fourth embodiment of the plasma-laser focusing unit 111D of the skin treatment device 200 as shown in FIG. 3C, the plasma-laser focusing unit 111D again comprises the centered anode 113 at least partially surrounded by a tubular cathode 114 forming the plasma channel 118 positioned in the center of the plasma-laser focusing unit 111D, similar to the embodiment in FIG. 3B. However, the laser beam shaping system 109 (not shown in FIG. 3C) now generates a plurality of laser beams 106a, 106b arranged around the plasma channel 118. The focusing system 112 now comprises a plurality of lenses 112a and 112b, which each focuses one of the plurality of laser beams 106a and 106b into the respective target positions 110a and 110b. When the plasma-laser focusing unit 111D according to the invention, for example, generates two laser beams 106a, 106b, the laser beams 106a and 106b, together with their associated lenses 112a and 112b, may be configured to rotate around the plasma channel 118 of the plasma-laser focusing unit 111D, for example, by means of a rotating lens tube holder 130, to provide rotational scanning of the plurality of laser beams 106a, 106b in the skin tissue 102. This may lead to the formation of lesions in a circular pattern. By configuring the skin treatment device 200 so as to additionally, for example, scan the focus of the laser beams 106a, 106b in a direction perpendicular to the skin surface 103, helical lesions may be formed inside the skin tissue 102.

Figure 4:
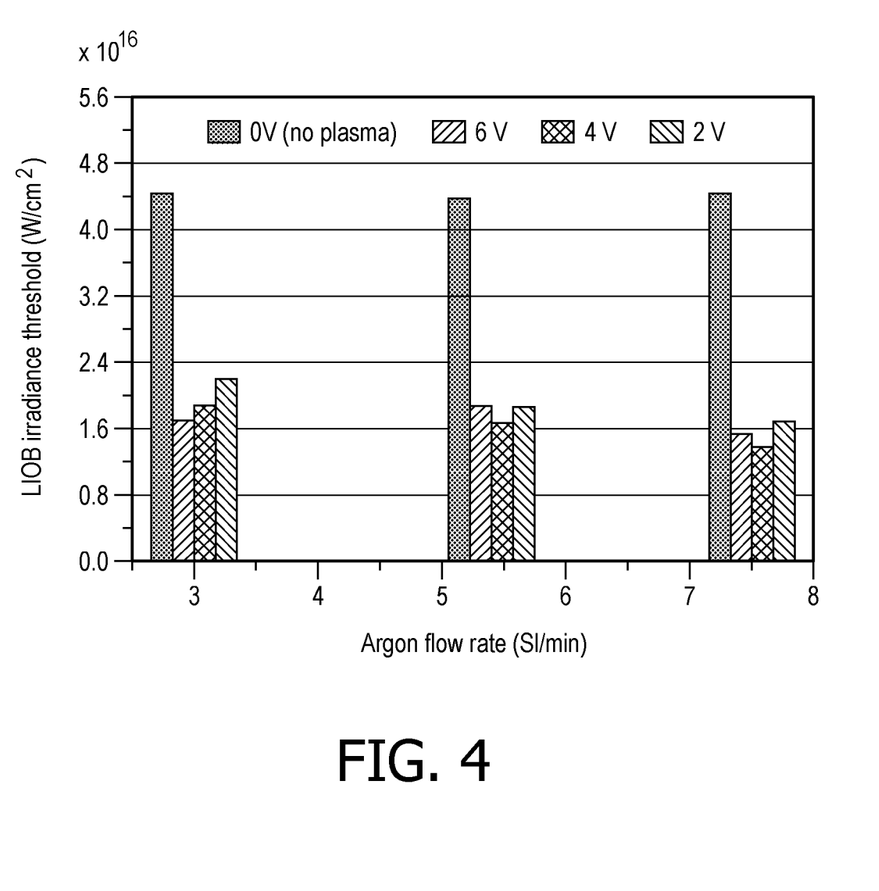
FIG. 4 shows measurement results comparing the laser power intensity threshold required for generating the light induced optical breakdown process with and without the use of plasma for different flow rates of Argon gas.

FIG. 4 shows measurement results comparing the irradiance threshold of the light induced optical breakdown (further also indicated as LIOB) process with and without the use of plasma for different flow rates of Argon gas. On the horizontal axis of the graph of FIG. 4, the different Argon flow rates are shown in three steps from 3 standard liter per minute via 5.4 standard liter per minute to 7.5 standard liter per minute. The vertical axis indicates a LIOB irradiance threshold necessary for creating the multiphoton ionization process inside the skin tissue 102. For each of the different Argon flow rates, a four-bar grouping of results is shown centered around the Argon flow rate. The black leftmost bar of each of the groupings indicates the laser beam intensity when no plasma 100 is used at the target position. The second, third and fourth bar from the left in each of the groupings indicates the required irradiance threshold in the presence of a plasma, the plasma being generated using different voltages (respectively 6 Volt, 4 Volt and 2 Volt).

The results shown in FIG. 4 are generated using a plasma unit 117 having a quartz capillary (inner diameter 1.6 mm) in which a centered electrode 113 (1 mm diameter) is mounted. In a continuous working mode, a high-frequency (HF) voltage (1.1 MHz, 2-6 kVpp) is coupled to the pin-type electrode 113. The plasma 100 is generated from the top of the centered electrode and expands to the surrounding air outside a nozzle. At maximum input DC power of 3.5 W, the ignited plasma jet has a length of up to 12 mm and free electron density is in the range of $10^{12}$ to $10^{14}$ $cm^{-3}$. Using such a plasma unit 117, it is shown that the laser pulse energy required for multiphoton ionization inside skin tissue 102 is reduced by up to 70%.

In summary, the invention provides a non-invasive skin treatment device 200 for generating a multiphoton ionization process at a target position 110 in skin tissue 102. The skin treatment device 200 comprises a laser source 105 configured and constructed for generating a treatment laser beam 106, an optical system 109, 112 for focusing the treatment laser beam 106 into the target position 110 below a skin surface 103, and a plasma unit 117 configured and constructed for generating a plasma 100 such that, in use, at least a portion of the plasma 100 penetrates the skin tissue 102 for generating at least one free electron at the target position 110. The skin treatment device further comprises a control unit 123 configured and constructed for controlling the laser source 105 and the plasma unit 117 such that, in use, at least a portion of the light of the treatment laser beam is absorbed by said at least one free electron at the target position 110, thereby generating the multiphoton ionization process. A result of the use of the plasma in generating the multiphoton ionization process is that the overall intensity of the treatment laser beam required to generate the multiphoton ionization process is reduced as compared to when the multiphoton ionization process is generated using a laser beam only.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A skin treatment device for generating a multiphoton ionization process in a target position in skin tissue, the skin treatment device comprising:
    a laser source configured and constructed for generating a treatment laser beam,
    an optical system configured and constructed such that, in use, the treatment laser beam is focused into a focal spot in the target position in the skin tissue,
    a plasma unit configured and constructed for generating a plasma such that, in use, at least a portion of the plasma penetrates the skin tissue and generates at least one free electron in the target position in the skin tissue, and
    a control unit configured and constructed for controlling the laser source and the plasma unit,
    characterized in that the laser source and the optical system are configured and constructed such that, in use, a power density (W/cm$^2$) of the treatment laser beam) in the focal spot in the skin tissue is below a first power density threshold ($I_{th1}$) for the skin tissue, above which a free electron is generated in the skin tissue by absorption of photons present in the treatment laser beam, and the power density (W/cm$^2$) of the treatment laser beam in the focal spot is above a second power density threshold ($I_{th2}$) for the skin tissue, above which an avalanche ionization process is generated in the skin tissue by Inverse Bremsstrahlung absorption by a free electron of photons present in the treatment laser beam.

2. The skin treatment device c according to claim 1, wherein the control unit is configured and constructed to activate the laser source to generate the treatment laser beam only after the plasma has been generated by the plasma unit.

3. The skin treatment device according to claim 1, wherein the skin treatment device further comprises an electric field generator controlled by the control unit, wherein the electric field generator is configured and constructed for generating, in use, an electric field to guide the plasma towards the target position.

4. The skin treatment device according to claim 3, wherein the control unit is configured and constructed for adjusting a strength of the electric field generated by the electric field generator in order to achieve a desired penetration depth and/or a desired penetration speed of the plasma towards the target position.

5. The skin treatment device according to claim 1, wherein the plasma unit comprises a plasma channel in which the plasma is generated, and wherein, in use, a fluid flows through the plasma channel towards a skin surface, at least a portion of the fluid being converted into the plasma in the plasma channel.

6. The skin treatment device according to claim 5, wherein the plasma channel comprises an outlet for emitting the plasma towards the skin surface, the outlet being configured and constructed for directing the plasma towards the target position.

7. The skin treatment device according to claim 5, wherein the fluid comprises a noble gas.

8. The skin treatment device according to claim 1, wherein the plasma unit comprises plasma generation means at or near a skin surface for generating the plasma at or near the skin surface.

9. The skin treatment device according to claim 1, wherein the plasma unit is configured to generate a direct plasma, an indirect plasma and/or a hybrid plasma.

10. The skin treatment device according to claim 1, wherein the plasma generated by the plasma unit comprises a non-thermal plasma.

11. The skin treatment device according to claim 1, wherein the optical system is configured and constructed to generate a plurality of focal spots in a plurality of target positions inside the skin tissue, the plasma unit being configured and constructed to generate the plasma near a skin surface such that, in use, at least a portion of the plasma penetrates the skin tissue for generating at least one free electron in each of said plurality of target positions.

12. The skin treatment device according to claim 11, wherein the skin treatment device comprises more than one plasma.

13. The skin treatment device according to claim 1, wherein the target position is between 0 and 2 mm below a skin surface, or wherein the target position is between 0.5 and 1.5 mm below a skin surface.

* * * * *